US012788401B2

(12) United States Patent
Yang et al.

(10) Patent No.: US 12,788,401 B2
(45) Date of Patent: Nov. 10, 2026

(54) STAPLING SURGICAL INSTRUMENT AND A METHOD FOR OPERATING A STAPLING SURGICAL INSTRUMENT

(71) Applicants: EZISURG (SUZHOU) MEDICAL CO., LTD., Suzhou (CN); EZISURG MEDICAL CO., LTD., Shanghai (CN)

(72) Inventors: Guang Yang, Shanghai (CN); Chuangang Tang, Shanghai (CN); Honglin Nie, Shanghai (CN)

(73) Assignees: EZISURG (SUZHOU) MEDICAL CO., LTD., Suzhou (CN); EZISURG MEDICAL CO., LTD., Shanghai (CN)

( * ) Notice: Subject to any disclaimer, the term of this patent is extended or adjusted under 35 U.S.C. 154(b) by 0 days.

(21) Appl. No.: 19/354,284

(22) Filed: Oct. 9, 2025

(65) Prior Publication Data

US 2026/0102160 A1 Apr. 16, 2026

(30) Foreign Application Priority Data

Oct. 14, 2024 (CN) ........................ 202411433511.2

(51) Int. Cl.
*A61B 17/072* (2006.01)
*A61B 17/00* (2006.01)

(52) U.S. Cl.
CPC .................. *A61B 17/07207* (2013.01); *A61B 2017/00022* (2013.01); *A61B 2017/00398* (2013.01)

(58) Field of Classification Search
CPC .... A61B 17/07207; A61B 2017/00017; A61B 2017/00022; A61B 2017/00398; A61B 2017/00473; A61B 2017/2923; A61B 2017/2927
See application file for complete search history.

(56) References Cited

U.S. PATENT DOCUMENTS

| | | | | | |
|---|---|---|---|---|---|
| 4,287,655 | A * | 9/1981 | Gerkey | G05B 19/414 | 165/76 |
| 5,579,899 | A * | 12/1996 | Arnold | H01H 13/18 | 200/47 |
| 6,605,793 | B2 * | 8/2003 | Banfield | H01H 15/107 | 200/16 R |
| 2002/0134811 | A1 * | 9/2002 | Napier | B24B 23/04 | 227/134 |
| 2014/0110456 | A1 * | 4/2014 | Taylor | A61B 90/90 | 227/176.1 |

(Continued)

*Primary Examiner* — Thomas M Wittenschlaeger
(74) *Attorney, Agent, or Firm* — Fox Rothschild LLP

(57) ABSTRACT

A stapling surgical instrument includes a handle assembly, a shaft assembly, and a plurality of loading units with different staple line lengths; the handle assembly includes a control circuit provided with mounting sensor switches and a slider, the shaft assembly includes a sensing mechanism, any one of the loading units is releasably mounted to the shaft assembly; the mounting of the loading unit drives the sensing mechanism to push the slider, the slider actuates any one of the mounting sensor switches to generate a first signal or does not actuate to generate a second signal, and the control circuit identifies whether the loading unit is not mounted or identifies the staple line length based on all combinations of the first signals or the second signals. Reducing the number of the mounting sensor switches saves space, facilitating their installation in the handle assembly.

10 Claims, 24 Drawing Sheets

(56) References Cited

U.S. PATENT DOCUMENTS

| | | | | |
|---|---|---|---|---|
| 2014/0252063 | A1* | 9/2014 | Ross | A61B 90/98<br>227/175.1 |
| 2015/0351765 | A1* | 12/2015 | Valentine | A61B 17/07207<br>227/176.1 |
| 2017/0196560 | A1* | 7/2017 | Leimbach | A61B 17/072 |
| 2017/0245854 | A1* | 8/2017 | Zemlok | A61B 17/07207 |
| 2019/0060025 | A1* | 2/2019 | Pantazis | A61B 90/08 |
| 2019/0290265 | A1* | 9/2019 | Shelton, IV | G16H 40/63 |
| 2021/0290235 | A1* | 9/2021 | Richard | A61B 17/07207 |
| 2022/0167973 | A1* | 6/2022 | Shelton, IV | A61B 17/072 |
| 2024/0164781 | A1* | 5/2024 | Yang | A61B 17/07207 |

* cited by examiner

STAPLING SURGICAL INSTRUMENT AND A METHOD FOR OPERATING A STAPLING SURGICAL INSTRUMENT

CROSS-REFERENCE TO RELATED APPLICATIONS

The disclosure is based upon and claims priority to Chinese Patent Application No. 202411433511.2, filed on Oct. 14, 2024, the entire contents of which are incorporated herein by reference.

TECHNICAL FIELD

The present disclosure relates to a surgical instrument, in particular to a stapling surgical instrument and a method for operating a stapling surgical instrument.

BACKGROUND

With the development of technology, open surgery has gradually transitioned to endoscopic surgery, and endoscopic staplers have progressively shifted from manual firing to motor-driven firing. Depending on the design, endoscopic staplers generally have two main types: one that replaces loading units with different staple line lengths, and another that replaces staple cartridges. During a surgical procedure, a single stapler may need to be loaded with multiple loading units sequentially to perform tissue stapling and cutting. The easyEndo universal endoscopic cutting stapler loads staple cartridges with staple line lengths of 30 mm, 45 mm, and 60 mm. A stapler that replaces loading units has the following advantages: the same stapler can replace loading units during a surgical procedure, effectively reducing surgical time and lowering surgical costs.

In the era of manual firing, when a stapler is equipped with loading units of different staple line lengths, a user determines the firing stroke and stops and retracts after completing the firing. However, when the above design is applied to an endoscopic stapler with motor-driven firing, since the control circuit cannot determine the staple line length of the loading unit and cannot precisely control the firing stroke, it may result in insufficient or excessive firing stroke during use, potentially causing damage to the stapler or harm to the patient. Therefore, a stapler capable of identifying loading units with different staple line lengths is required, which may control the firing stroke of the stapler based on the staple line length of the loading unit to ensure better performance of the stapler.

SUMMARY

The present disclosure aims to solve the problem that in existing stapling surgical instruments, space within a handle assembly is limited, and mounting sensor switches occupies a certain amount of space.

In one aspect of the present disclosure, a stapling surgical instrument includes a handle assembly, a shaft assembly, and a plurality of loading units with different staple line lengths; wherein the handle assembly includes a control circuit provided with mounting sensor switches and a slider, the shaft assembly includes a sensing mechanism, and any one of the loading units is configured to be releasably mounted to the shaft assembly; the number of the mounting sensor switches is less than the number of staple line lengths of the loading units; a mounting of the loading unit is configured to drive the sensing mechanism to push the slider, the slider is configured to actuate any one of the mounting sensor switches to generate a first signal or does not actuate to generate a second signal, and the control circuit is configured to identify whether the loading unit is not mounted or identifies the staple line length of the loading unit based on all combinations of the first signals or the second signals.

In one aspect of the present disclosure, a method for operating a stapling surgical instrument includes: providing a handle assembly, a shaft assembly, and a plurality of loading units with different staple line lengths; connecting the handle assembly to the shaft assembly, wherein the handle assembly includes a control circuit provided with mounting sensor switches and a slider, and the shaft assembly includes a sensing mechanism; releasably mounting any one of the loading units to the shaft assembly, wherein the number of the mounting sensor switches is less than the number of staple line lengths of the loading units; pushing the slider through the sensing mechanism to actuate any one of the mounting sensor switches to generate a first signal or not to actuate to generate a second signal; identifying whether the loading unit is not mounted or identifying the staple line length of the loading unit based on all combinations of the first signals or the second signals by the control circuit.

Space within the handle assembly is limited, and the mounting sensor switch occupies a certain amount of space. Reducing the number of the mounting sensor switches saves space, facilitating their installation in the handle assembly. Additionally, the control circuit fully utilizes all combinations of the first signals or the second signals.

BRIEF DESCRIPTION OF THE DRAWINGS

To enable people to intuitively and visually understand each technical feature and the overall technical solution of the present disclosure, the drawings supplement the description in the text of the embodiments with illustrations.

Figure 13A:
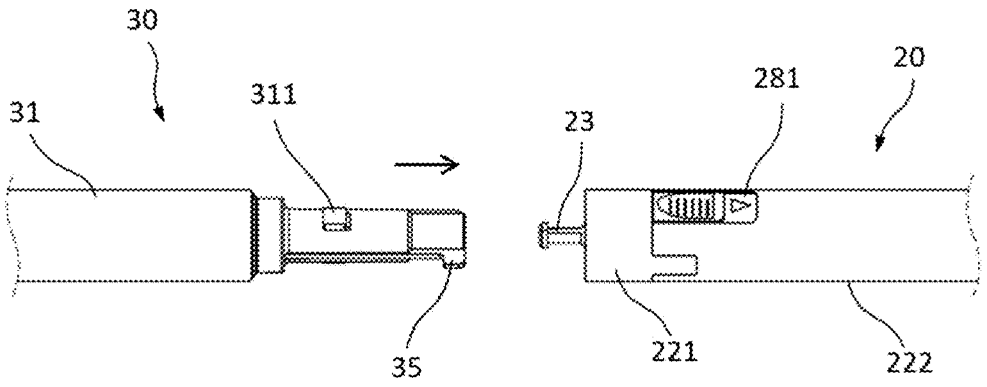
Figure 13B:
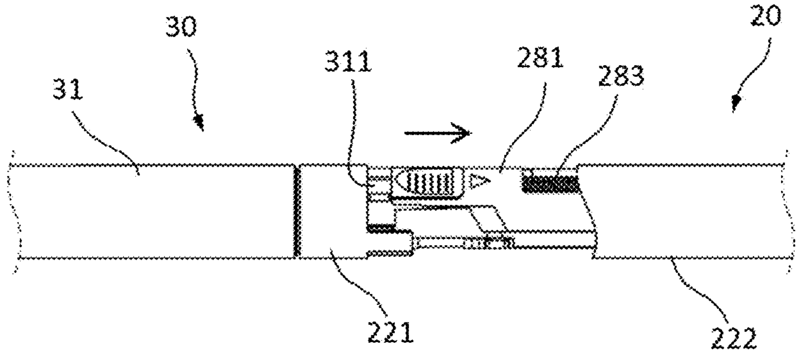
Figure 13C:
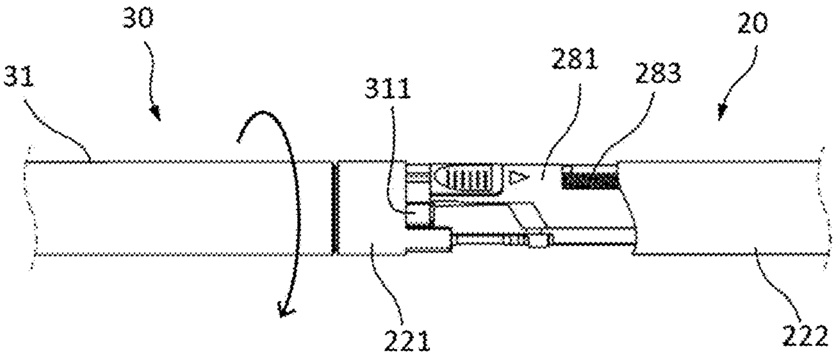
Figure 13D:
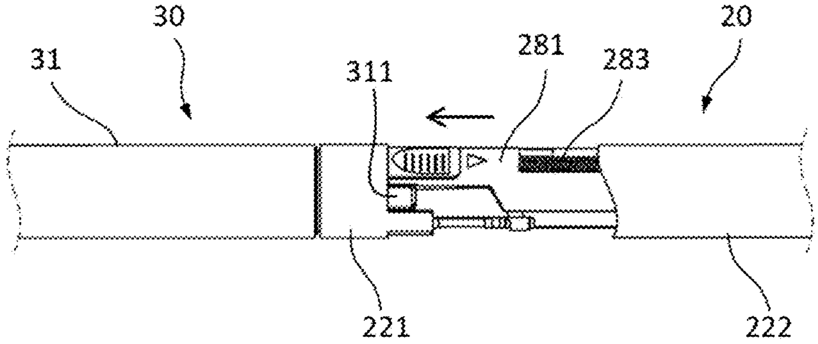
Figure 14A:
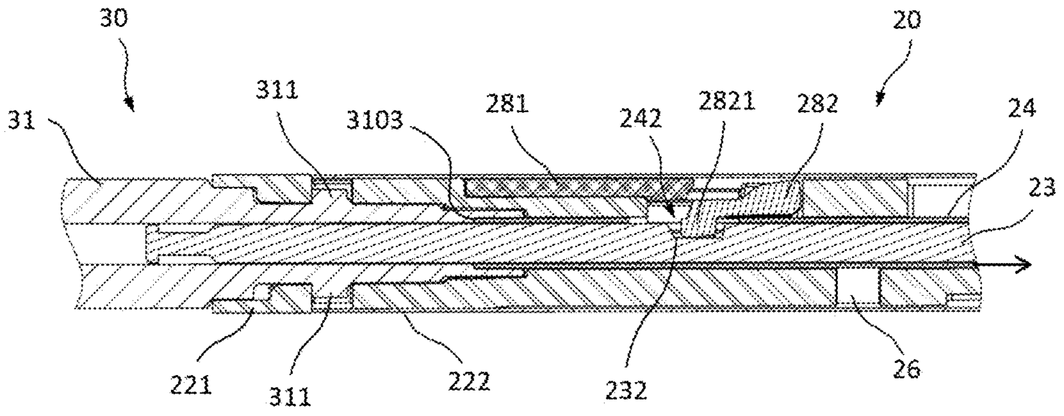
Figure 14B:
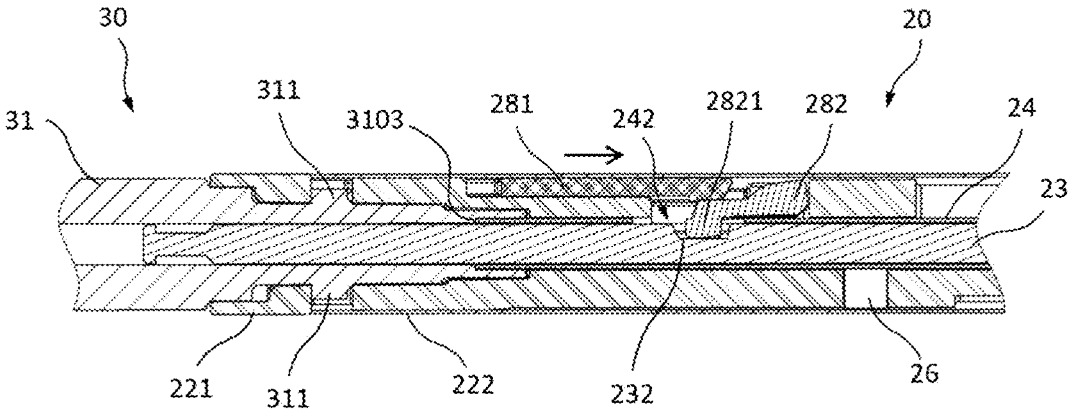
Figure 14C:
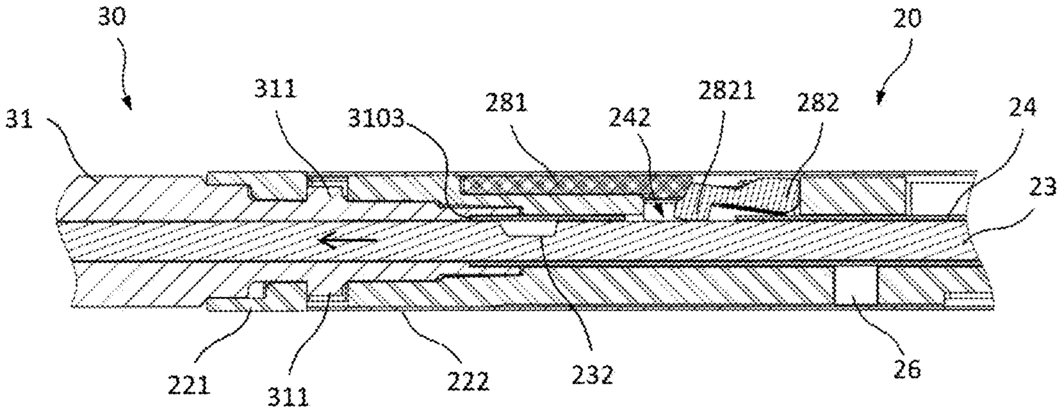
Figure 15:
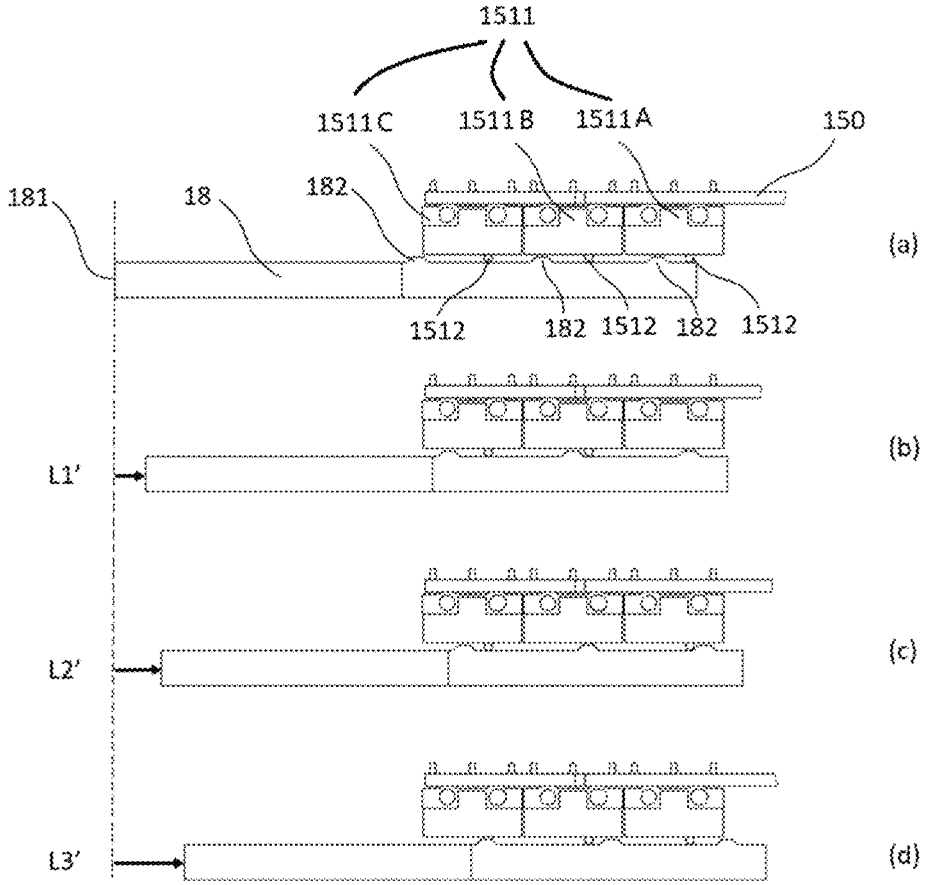
Figure 16:
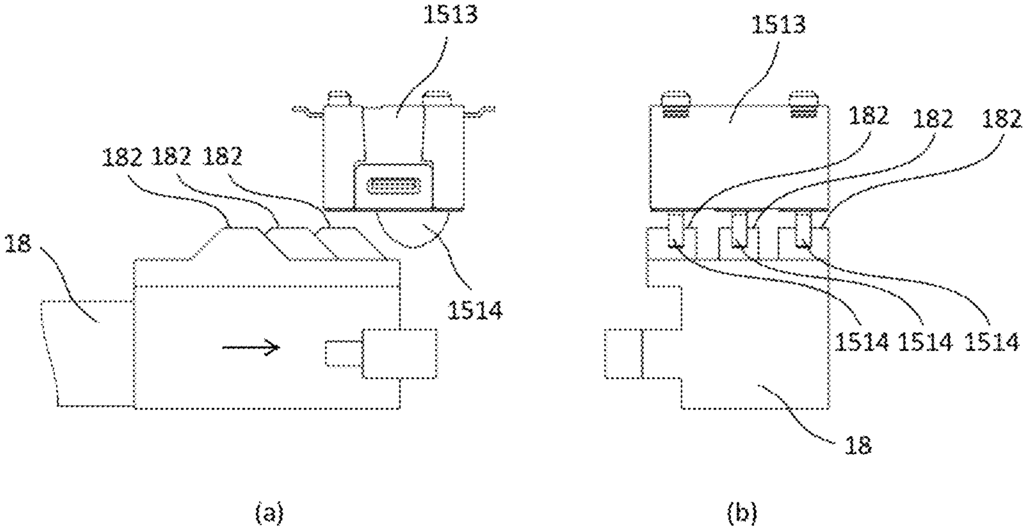
Figure 17:
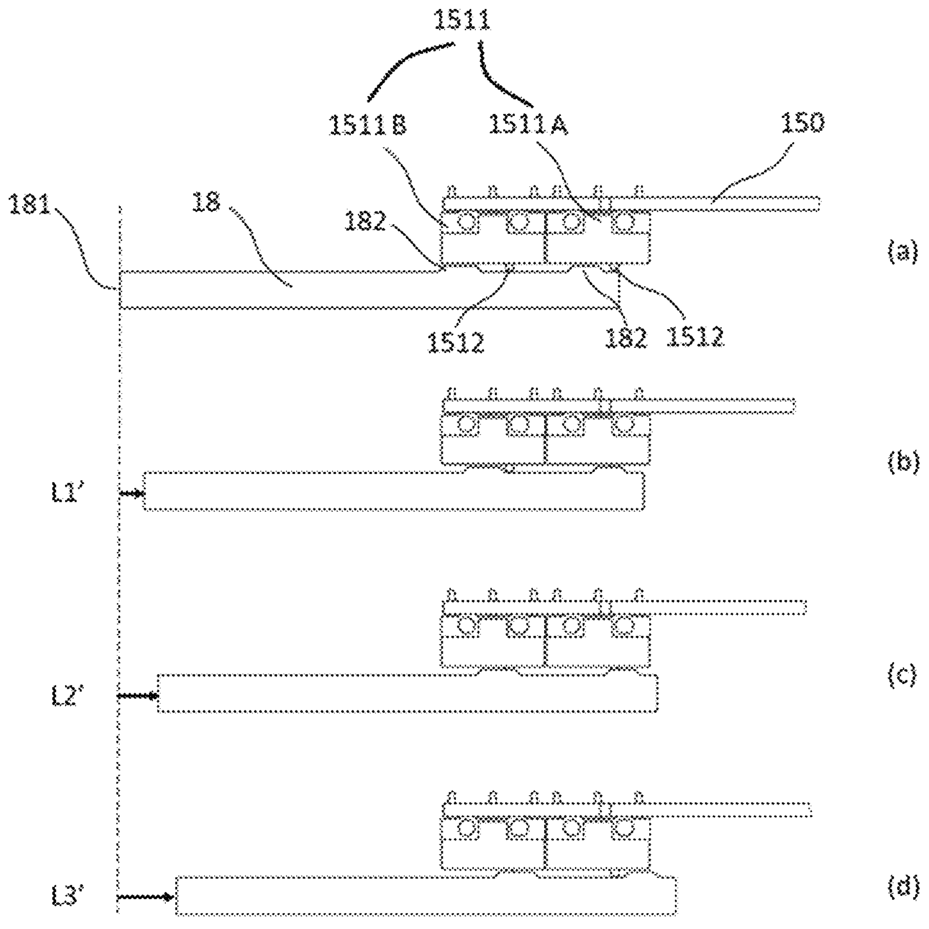
Figure 18:
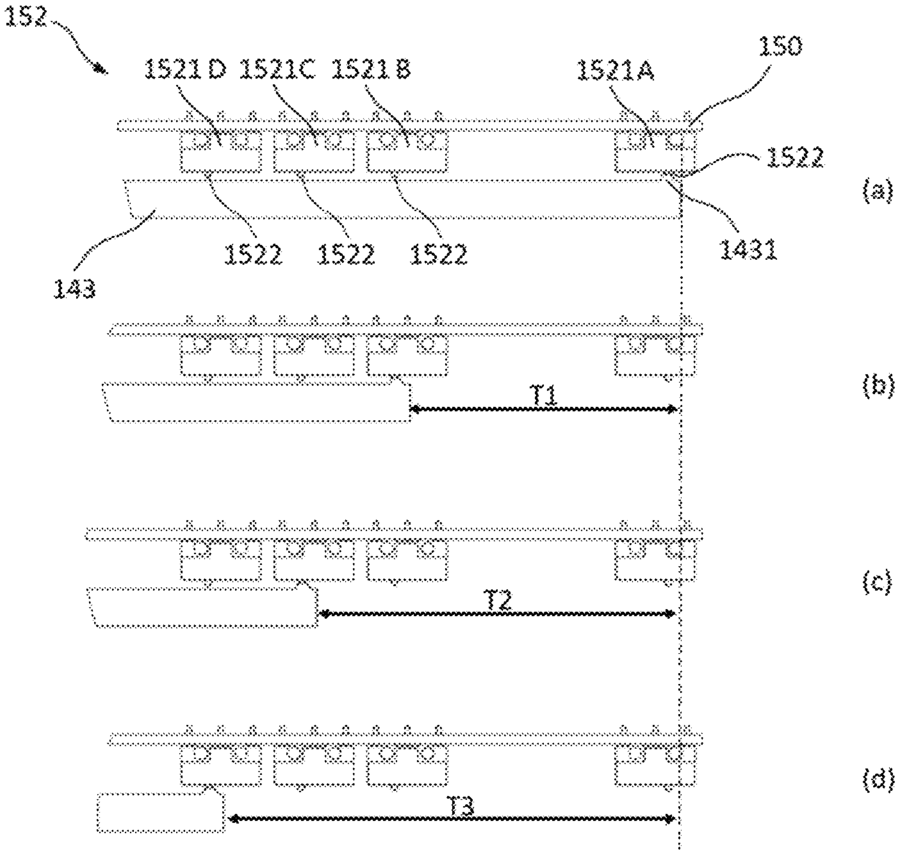
Figure 19:
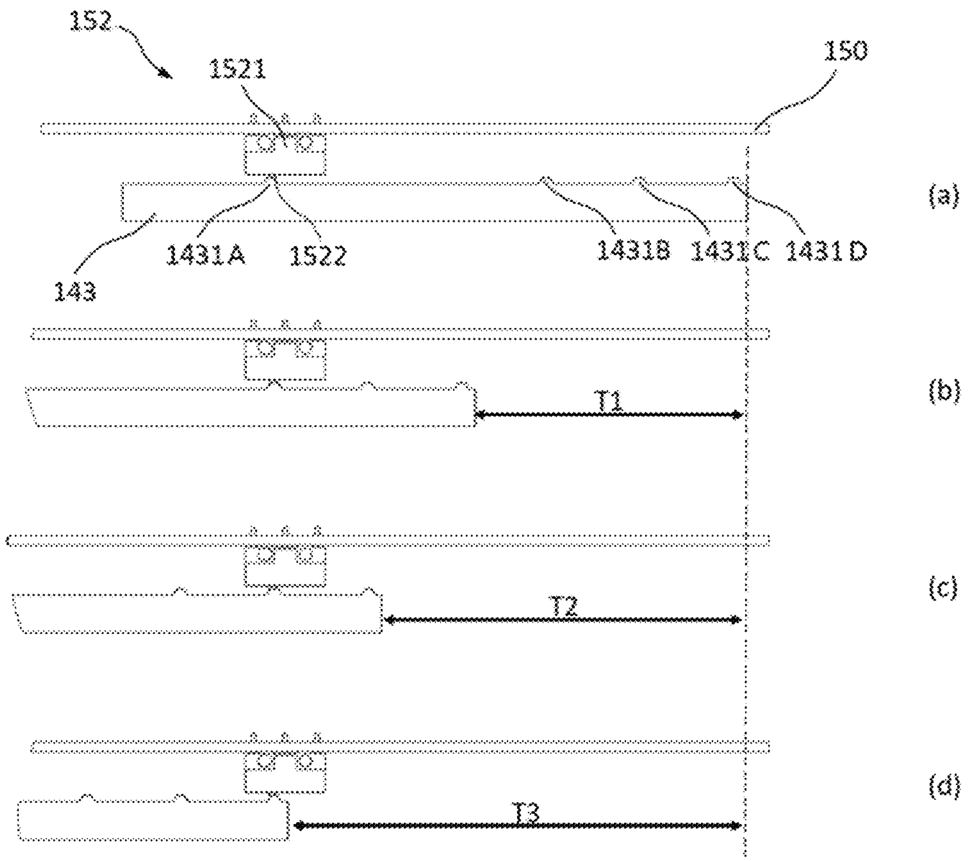

FIG. **13*a*** is an exemplary partial perspective view with the loading unit not mounted;

FIG. **13*b*** is an exemplary partial perspective view of moving the loading unit;

FIG. **13*c*** is an exemplary partial perspective view of rotating the loading unit;

FIG. 13*d* is an exemplary partial perspective view of removing the loading unit;

FIG. 14*a* is an exemplary cross-sectional view of the firing lever in the unlocked state;

FIG. 14*b* is an exemplary cross-sectional view of the firing lever in the locked state;

FIG. 14*c* is an exemplary cross-sectional view of moving the firing lever;

FIG. 15 is an exemplary perspective view of the mounting sensor module;

FIG. 16 is another exemplary perspective view of the mounting sensor module;

FIG. 17 is yet another exemplary perspective view of the mounting sensor module;

FIG. 18 is an exemplary perspective view of the displacement sensor module;

FIG. 19 is another exemplary perspective view of the displacement sensor module.

DETAILED DESCRIPTION

It should be understood that the exemplary embodiments described in the present disclosure are to be considered merely descriptive and not for the purpose of limitation.

The description of features or aspects in each exemplary embodiment should generally be considered applicable to similar features or aspects in other exemplary embodiments.

Figure 1:
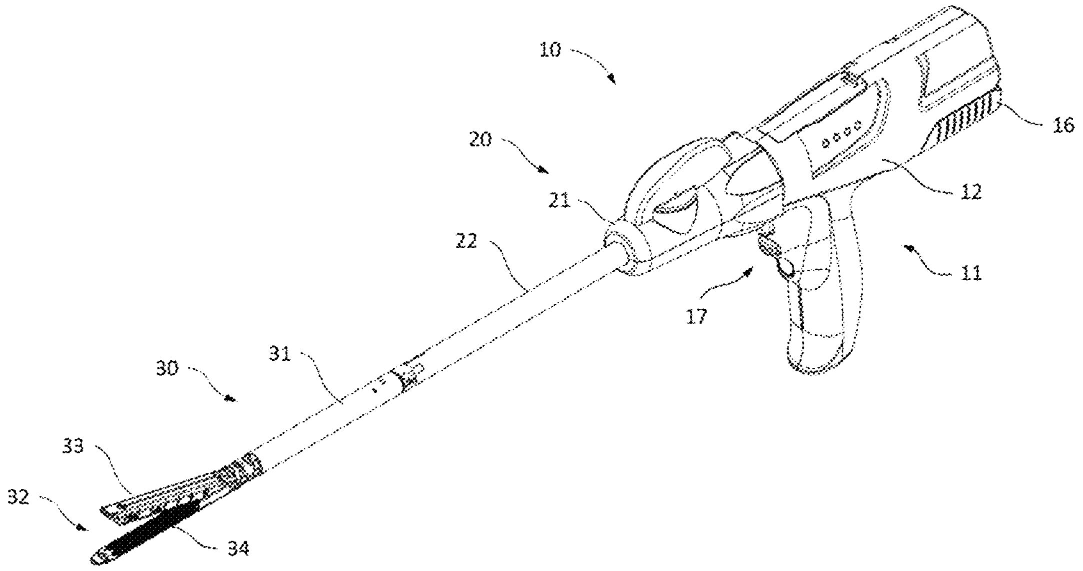
FIG. 1 is a perspective view of an exemplary stapling surgical instrument.
Figure 2:
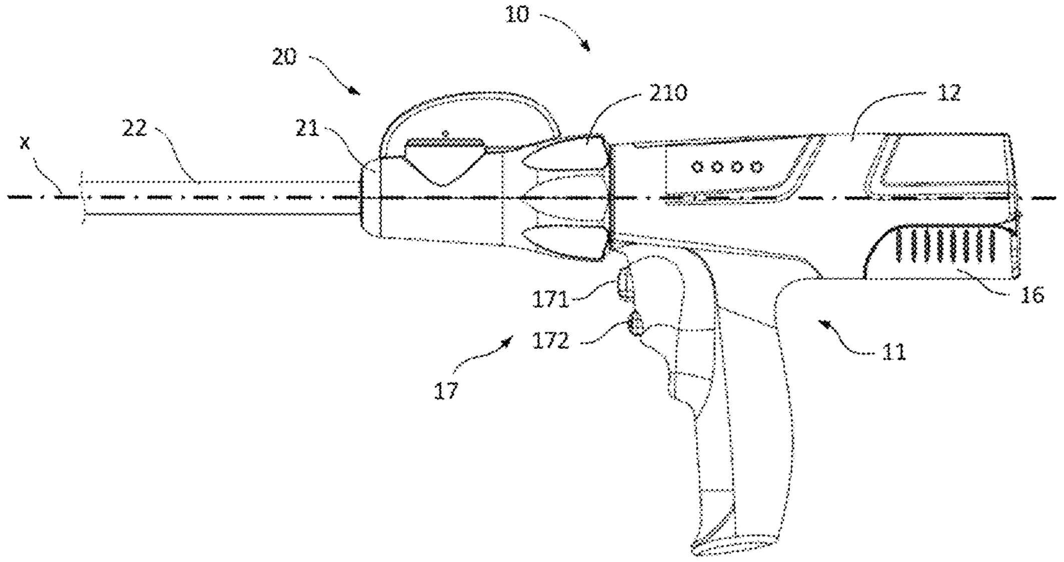
FIG. 2 is a perspective view of the handle assembly shown in FIG. 1.
Figure 3:
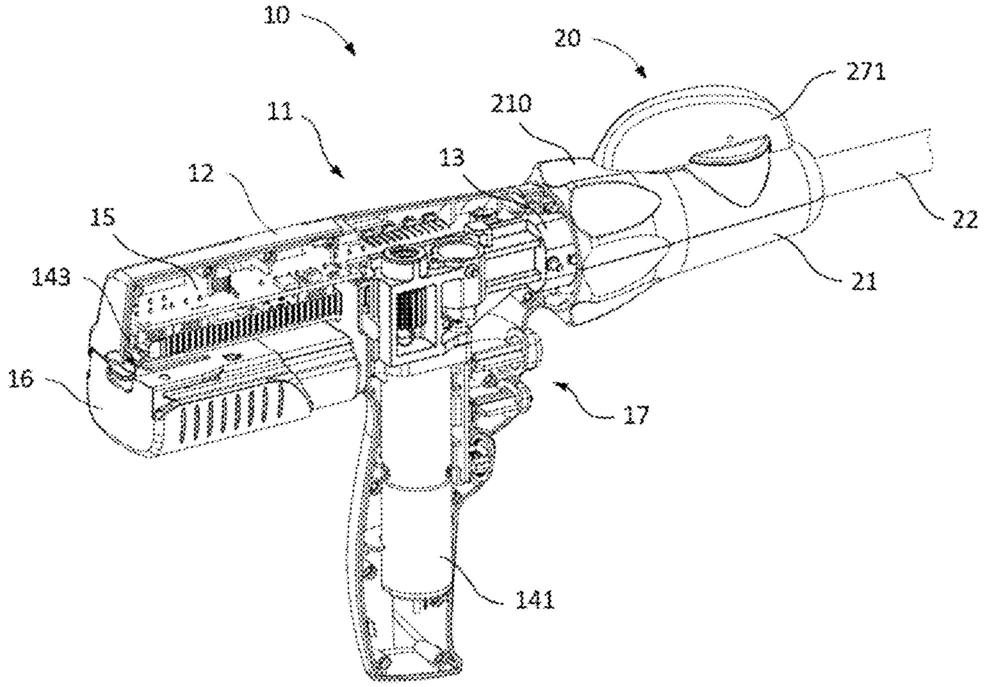
FIG. 3 is a partial perspective view of the handle assembly shown in FIG. 2.
Figure 4:
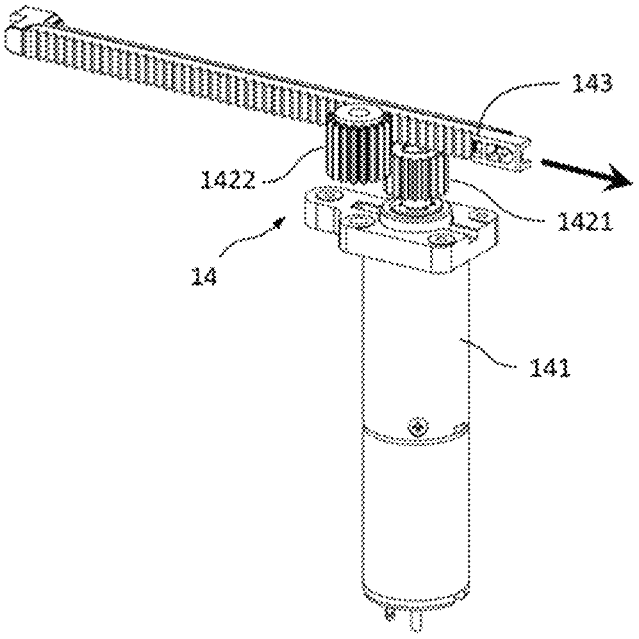
FIG. 4 is a perspective view of a drive assembly shown in FIG. 3.

As shown in FIG. 1 to FIG. 2, the stapling surgical instrument 10 includes a handle assembly 11, a shaft assembly 20, and a loading unit 30. The shaft assembly 20 defines a longitudinal axis x, and the longitudinal axis x extends from a proximal end to a distal end. A proximal end of the shaft assembly 20 is rotatably connected to a distal end of the handle assembly 11, and a proximal end of the loading unit 30 is releasably connected to a distal end of the shaft assembly 20. When the shaft assembly 20 rotates relative to the handle assembly 11, the loading unit 30 is capable of rotating with the shaft assembly 20.

As shown in FIG. 1 to FIG. 4 and FIG. 8 to FIG. 9, the handle assembly 11 includes a handle housing 12, a frame 13, a drive assembly 14, a control circuit 15, a power source 16, and a control button 17. The handle housing 12 secures the frame 13, the frame 13 includes an annular guide rail 131, the annular guide rail 131 connects to the shaft assembly 20, and the annular guide rail 131 provides rotational freedom for the shaft assembly 20. The drive assembly 14 includes a motor 141, a first gear 1421, a second gear 1422, and a rack 143. The first gear 1421 is mounted on an output shaft of the motor 141, the second gear 1422 engages with the first gear 1421, and the rack 143 engages with the second gear 1422. The motor 141 is fixed to the frame 13, the frame 13 provides a rotation axis for the second gear 1422, and the frame 13 provides a guide rail for the rack 143. When the motor 141 drives the rack 143 to move along the longitudinal axis x, the rack 143 moves from one of the proximal end or the distal end to the other. The control circuit 15 is fixed to the frame 13 or the handle housing 12, and the control circuit 15 is configured to control the rotation of the motor 141. The power source 16 may be a battery pack or a source of grid power, providing electrical energy for the stapling surgical instrument 10. The battery pack enables portability of the stapling surgical instrument 10. The control button 17 includes a forward button 171 and a reverse button 172. When a user presses the forward button 171, the control circuit 15 controls the motor 141 to drive the rack 143 to move from the proximal end to the distal end. When the user presses the reverse button 172, the control circuit 15 controls the motor 141 to drive the rack 143 to move from the distal end to the proximal end.

Figure 5:
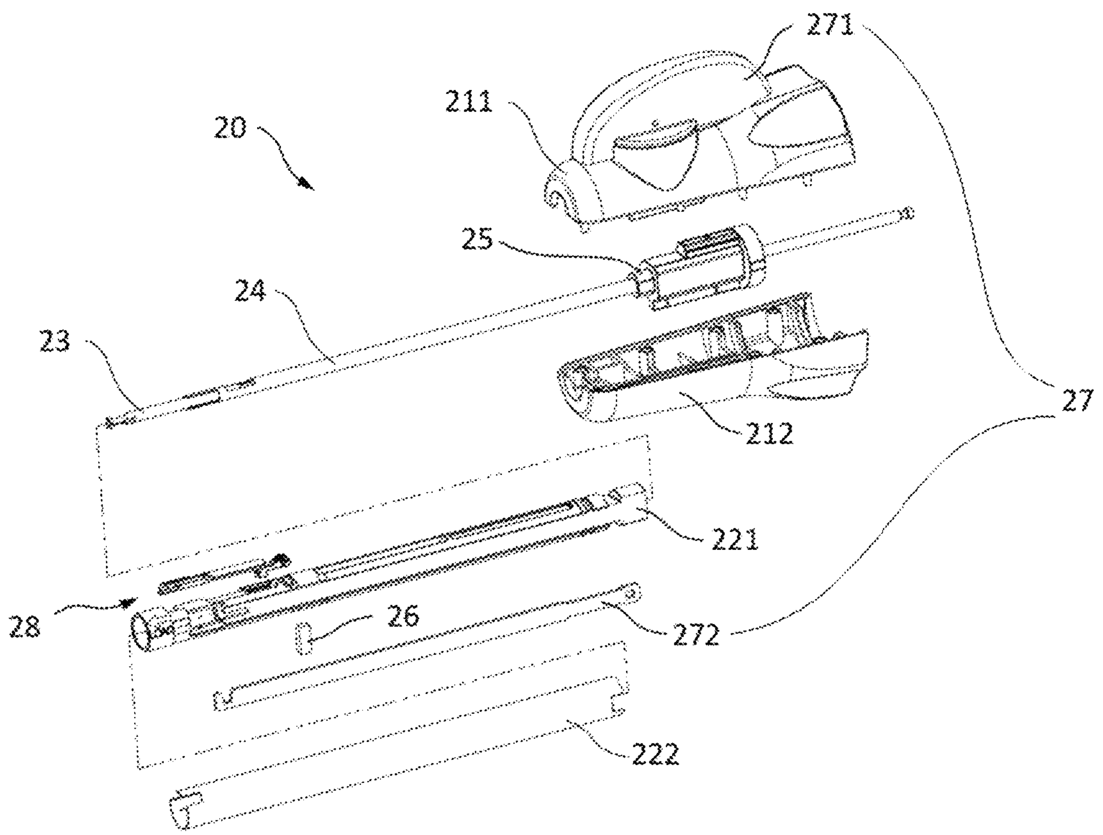
FIG. 5 is an exploded view of the shaft assembly shown in FIG. 1.
Figure 6:
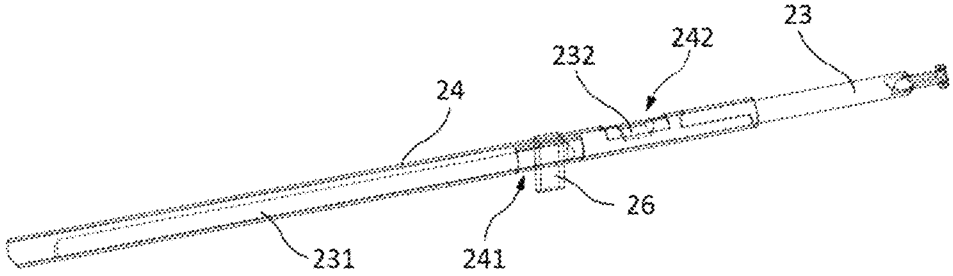
FIG. 6 is a partial perspective view of an elongated body shown in FIG. 5.

As shown in FIG. 5 to FIG. 6, the shaft assembly 20 includes a rotating housing 21 and an elongated body 22. The distal end of the rotating housing 21 is connected to the proximal end of the elongated body 22. The rotating housing 21 includes a first rotating housing 211 and a second rotating housing 212. The first rotating housing 211 is connected to the second rotating housing 212. The elongated body 22 includes a body portion 221 and an outer sleeve 222. The first rotating housing 211 and the second rotating housing 212 secure the body portion 221. The outer sleeve 222 surrounds the body portion 221, and the outer sleeve 222 and the body portion 221 are arranged coaxially.

Figure 10:
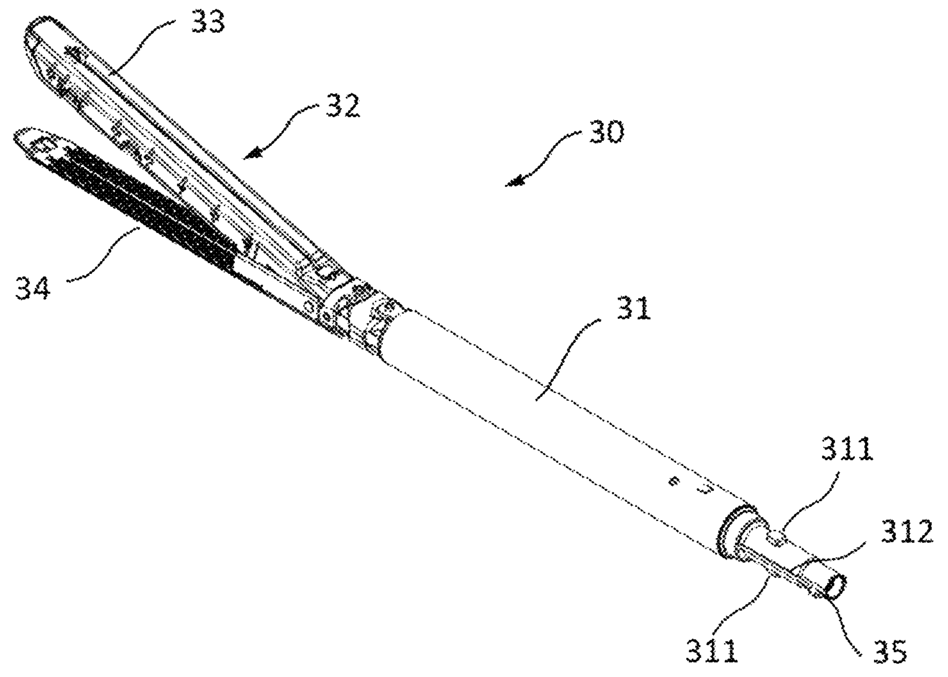
FIG. 10 is a perspective view of the loading unit shown in FIG. 1.

As shown in FIG. 10, the loading unit 30 includes a body portion 31 and a jaw assembly 32. The distal end of the body portion 31 is connected to the proximal end of the jaw assembly 32. The jaw assembly 32 includes a staple cartridge assembly 33 and an anvil assembly 34. The staple cartridge assembly 33 opens or closes relative to the anvil assembly 34. Staples in the staple cartridge assembly 33 can be ejected to the anvil assembly 34 for forming. The loading unit 30 is the first loading unit 30A, the second loading unit 30B, or the third loading unit 30C. The staple line length of the first loading unit 30A is 60 millimeters. The staple line length of the second loading unit 30B is 45 millimeters. The staple line length of the third loading unit 30C is 30 millimeters. The first loading unit 30A, the second loading unit 30B, or the third loading unit 30C can be respectively mounted on the shaft assembly 20.

As shown in FIG. 5, the shaft assembly 20 includes a bending control mechanism 27, and the bending control mechanism 27 includes a bending control wrench 271 and a first bending control rod 272; the loading unit 30 includes a second bending control rod 35. The bending control wrench 271 is disposed on the first rotating housing 211, and the first bending control rod 272 is disposed together with the body portion 221. A distal groove of the first bending control rod 272 connects to a proximal hook of the second bending control rod 35. When a user rotates the bending control wrench 271, the bending control wrench 271 drives the first bending control rod 272 to move along the longitudinal axis x. When the loading unit 30 is mounted to the shaft assembly 20, the first bending control rod 272 is capable of driving the second bending control rod 35 to enable bending of the jaw assembly 32.

Figure 8:
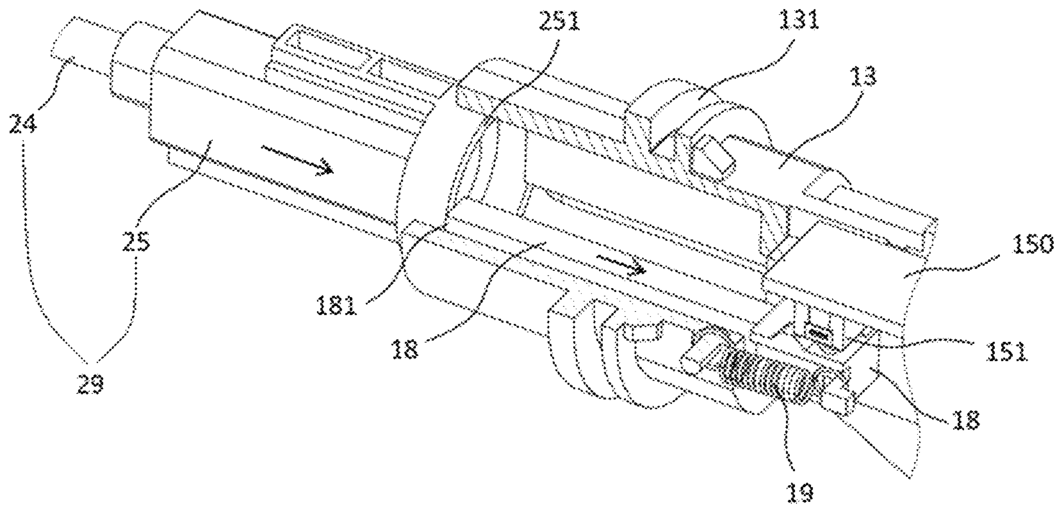
FIG. 8 is a partial perspective view of a rotating housing shown in FIG. 5.
Figure 9:
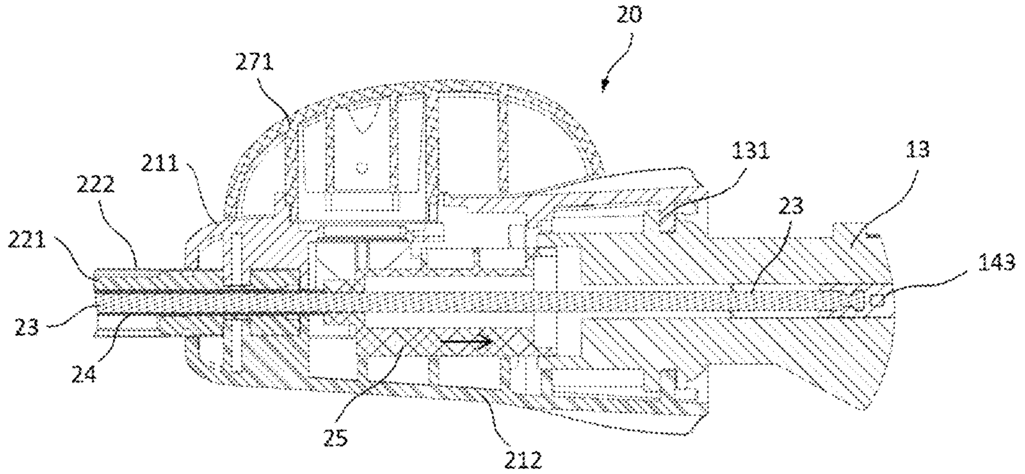
FIG. 9 is a cross-sectional view of the rotating housing shown in FIG. 8.

As shown in FIG. 8, the shaft assembly 20 includes a sensing mechanism 29, and the sensing mechanism 29 includes a sensing collar 24 and a sensing sleeve 25. The sensing collar 24 and the sensing sleeve 25 are disposed along the longitudinal axis x. The proximal end of the sensing collar 24 contacts the distal end of the sensing sleeve 25. The handle assembly 11 includes a slider 18 and a biasing member 19. The biasing member 19 may be an elastic member, such as a tension spring, a compression spring, a torsion spring, or an elastic clip. The biasing member 19 is capable of biasing the slider 18 toward a distal position, thereby causing the sensing sleeve 25 and the sensing collar 24 to move distally. A distal end 181 of the slider 18 contacts the proximal end of the sensing sleeve 25. The proximal end of the sensing sleeve 25 is an annular flange 251. When the loading unit 30 is mounted to the shaft assembly 20, the loading unit 30 pushes the sensing collar 24 to move proximally, and the sensing collar 24 pushes the sensing sleeve 25 to move proximally. Meanwhile, the sensing sleeve 25 pushes the slider 18 to move proximally.

As shown in FIG. 15 to FIG. 17, the control circuit 15 includes a circuit board 150, the circuit board 150 includes a mounting sensor module 151, and the mounting sensor module 151 includes mounting sensor switches 1511. The mounting sensor switches 1511 may include a button 1512, or may be a photoelectric switch or a Hall switch. Meanwhile, the slider 18 includes a protrusion 182, the protrusion 182 is capable of pressing the button 1512, or the slider 18 includes a recess, the recess is capable of releasing the button 1512, thereby enabling the control circuit 15 to identify the staple line length of the loading unit 30.

As shown in FIG. 15, a mounting sensor module 151 includes three mounting sensor switches 1511, wherein a first switch 1511A, a second switch 1511B, and a third switch 1511C are disposed from the proximal end to the distal end. Meanwhile, the slider 18 includes three protrusions 182, wherein a first protrusion 182, a second protrusion 182, and a third protrusion 182 are disposed from the proximal end to the distal end. When the loading unit 30 is not mounted to the shaft assembly 20, the biasing member 19 biases the slider 18 toward a distal position, and the protrusions 182 do not press the mounting sensor switches 1511. Thus, the control circuit 15 detects that the loading unit 30 is not mounted. When the first loading unit 30A is mounted to the shaft assembly 20, the sensing mechanism 29 pushes the slider 18 to move a distance L1', and the first protrusion 182 presses the first switch 1511A. Thus, the control circuit 15 identifies the staple line length of the first loading unit 30A. When the second loading unit 30B is mounted to the shaft assembly 20, the sensing mechanism 29 pushes the slider 18 to move a distance L2', and the second protrusion 182 presses the second switch 1511B. Thus, the control circuit 15 identifies the staple line length of the second loading unit 30B. When the third loading unit 30C is mounted to the shaft assembly 20, the sensing mechanism 29 pushes the slider 18 to move a distance L3', and the third protrusion 182 presses the third switch 1511C. Thus, the control circuit 15 identifies the staple line length of the third loading unit 30C.

As shown in FIG. 16, another mounting sensor module 151 includes mounting sensor switches 1513, the mounting sensor switches 1513 includes three buttons 1514, wherein a first button 1514, a second button 1514, and a third button 1514 are disposed from the proximal end to the distal end and are offset in a direction perpendicular to the longitudinal axis x. Meanwhile, the slider 18 includes three protrusions 182, wherein a first protrusion 182, a second protrusion 182, and a third protrusion 182 are disposed from the proximal end to the distal end and are offset in a direction perpendicular to the longitudinal axis x. When a loading unit 30 is mounted to the shaft assembly 20, the sensing mechanism 29 pushes the slider 18 to move, and one protrusion 182 presses one button 1514. Thus, the control circuit 15 identifies the staple line length of the loading unit 30.

As shown in FIG. 17, another mounting sensor module 151 includes two mounting sensor switches 1511, wherein the first switch 1511A and the second switch 1511B are disposed from the proximal end to the distal end. Meanwhile, the slider 18 includes two protrusions 182, wherein a first protrusion 182 and a second protrusion 182 are disposed from the proximal end to the distal end. When the loading unit 30 is not mounted to the shaft assembly 20, the first protrusion 182 does not press the first switch 1511A, and the second protrusion 182 does not press the second switch 1511B. The mounting sensor module 151 generates a combination of a second signal and a second signal. Thus, the control circuit 15 detects that the loading unit 30 is not mounted. When the first loading unit 30A is mounted to the shaft assembly 20, the first protrusion 182 presses the first switch 1511A, and the second protrusion 182 does not press the second switch 1511B. The mounting sensor module 151 generates a combination of a first signal and a second signal. Thus, the control circuit 15 identifies the staple line length of the first loading unit 30A. When the second loading unit 30B is mounted to the shaft assembly 20, the first protrusion 182 presses the first switch 1511A, and the second protrusion 182 presses the second switch 1511B. The mounting sensor module 151 generates a combination of a first signal and a first signal. Thus, the control circuit 15 identifies the staple line length of the second loading unit 30B. When the third loading unit 30C is mounted to the shaft assembly 20, the first protrusion 182 does not press the first switch 1511A, and the second protrusion 182 presses the second switch 1511B. The mounting sensor module 151 generates a combination of a second signal and a first signal. Thus, the control circuit 15 identifies the staple line length of the third loading unit 30C.

In an embodiment, the stapling surgical instrument 10 includes a handle assembly 11, a shaft assembly 20, and a plurality of loading units 30 with different staple line lengths; the handle assembly 11 includes a control circuit 15 provided with mounting sensor switches 1511 and a slider 18, the shaft assembly 20 includes a sensing mechanism 29, and any loading unit 30 is releasably mounted to the shaft assembly 20; the number of the mounting sensor switches 1511 is less than the number of staple line lengths of the loading units 30; the mounting of the loading unit 30 drives the sensing mechanism 29 to push the slider 18, and the slider 18 actuates any mounting sensor switch 1511 to generate a first signal or does not actuate it, generating a second signal, and the control circuit 15 identifies whether the loading unit 30 is not mounted or determines the staple line length of the loading unit 30 based on all combinations of the first signals or the second signals. The space in the handle assembly 11 is limited, and the mounting sensor switches 1511 occupy a certain amount of space. Reducing the number of the mounting sensor switches 1511 saves space, facilitating their installation in the handle assembly 11. Additionally, the control circuit 15 fully utilizes all combinations of the first signals or the second signals.

Specifically, the mounting sensor switch 1511 is the first switch 1511A or the second switch 1511B; when the loading unit 30 is released from the shaft assembly 20, the slider 18 does not actuate the first switch 1511A and the second switch 1511B, and the control circuit 15 detects that the loading unit 30 is not mounted. The plurality of loading units 30 are the first loading unit 30A, the second loading unit 30B, or the third loading unit 30C. When the first loading unit 30A is mounted to the shaft assembly 20, the slider 18 actuates the first switch 1511A and does not actuate the second switch 1511B, and the control circuit 15 identifies the staple line length of the first loading unit 30A. When the second loading unit 30B is mounted to the shaft assembly 20, the slider 18 actuates the first switch 1511A and the second switch 1511B, and the control circuit 15 identifies the staple line length of the second loading unit 30B. When the third loading unit 30C is mounted to the shaft assembly 20, the slider 18 does not actuate the first switch 1511A and actuates the second switch 1511B, and the control circuit 15 identifies the staple line length of the third loading unit 30C. If either the first switch 1511A or the second switch 1511B is actuated, a first signal is generated. If either the first switch 1511A or the second switch 1511B is not actuated, a second signal is generated. Thus, the control circuit 15 fully utilizes four combinations of the first signal and the second signal.

As shown in FIG. 18 to FIG. 19, the circuit board 150 includes a displacement sensor module 152, and the displacement sensor module 152 includes a displacement sensor switch 1521. The displacement sensor switch 1521 may include a button 1522, or may be a photoelectric switch or a Hall switch. Meanwhile, the rack 143 includes a protrusion 1431, the protrusion 1431 is capable of pressing the button 1522, or the rack 143 is capable of first pressing the button 1522 and then releasing the button 1522 after movement, thus enabling the control circuit 15 to control the firing stroke of the loading unit 30.

As shown in FIG. 18, a displacement sensor module 152 includes four displacement sensor switches 1521, wherein a first switch 1521A, a second switch 1521B, a third switch 1521C, and a fourth switch 1521D are disposed from the proximal end to the distal end. Meanwhile, the proximal end of the rack 143 includes a protrusion 1431. When the rack 143 is at an initial position, the protrusion 1431 presses the first switch 1521A. When the motor 141 drives the rack 143 to reach a first displacement T1, the protrusion 1431 presses the second switch 1521B, and the first displacement T1 corresponds to the firing stroke of the third loading unit 30C. Thus, the control circuit 15 is capable of controlling the firing stroke of the third loading unit 30C. When the motor 141 drives the rack 143 to reach a second displacement T2, the protrusion 1431 presses the third switch 1521C, and the second displacement T2 corresponds to the firing stroke of the second loading unit 30B. Thus, the control circuit 15 is capable of controlling the firing stroke of the second loading unit 30B. When the motor 141 drives the rack 143 to reach a third displacement T3, the protrusion 1431 presses the fourth switch 1521D, and the third displacement T3 corresponds to the firing stroke of the first loading unit 30A. Thus, the control circuit 15 is capable of controlling the firing stroke of the first loading unit 30A.

As shown in FIG. 19, a displacement sensor module 152 includes a displacement sensor switch 1521. Meanwhile, the rack includes four protrusions 1431, wherein a first protrusion 1431A, a second protrusion 1431B, a third protrusion 1431C, and a fourth protrusion 1431D are disposed from the distal end to the proximal end. When the rack 143 is at the initial position, the first protrusion 1431A presses the displacement sensor switch 1521 to generate a first third signal. When the motor 141 drives the rack 143 to reach the first displacement T1, the second protrusion 1431B presses the displacement sensor switch 1521 to generate a second third signal, and the first displacement T1 corresponds to the firing stroke of the third loading unit 30C. Thus, the control circuit 15 is capable of controlling the firing stroke of the third loading unit 30C. When the motor 141 drives the rack 143 to reach the second displacement T2, the third protrusion 1431C presses the displacement sensor switch 1521 to generate a third third signal, and the second displacement T2 corresponds to the firing stroke of the second loading unit 30B. Thus, the control circuit 15 is capable of controlling the firing stroke of the second loading unit 30B. When the motor 141 drives the rack 143 to reach the third displacement T3, the fourth protrusion 1431D presses the displacement sensor switch 1521 to generate a fourth third signal, and the third displacement T3 corresponds to the firing stroke of the first loading unit 30A. Thus, the control circuit 15 is capable of controlling the firing stroke of the first loading unit 30A.

In an embodiment, the handle assembly 11 includes a rack 143 provided with a plurality of protrusions 1431, and the control circuit 15 includes a displacement sensor switch 1521. The rack 143 is movable between an initial position and a final position, the protrusions 1431 actuate the displacement sensor switch 1521 to generate a third signal or do not actuate the displacement sensor switch 1521 to generate a fourth signal, and the control circuit 15 detects the initial position or a displacement of the rack 143 based on the number of the third signals, the displacement of the rack 143 corresponding to the firing stroke of the loading unit 30. Thus, the control circuit 15 is capable of controlling the firing stroke of the loading unit 30. Additionally, the space in the handle assembly 11 is limited, and the displacement sensor switch 1521 occupies a certain amount of space. Reducing the number of the displacement sensor switches 1521 saves space, facilitating their installation in the handle assembly 11.

Specifically, the plurality of protrusions 1431 are the first protrusion 1431A, the second protrusion 14311B, the third protrusion 1431C, and the fourth protrusion 1431D. When the rack 143 is at the initial position, the first protrusion 1431A actuates the displacement sensor switch 1521 to generate the first third signal, and the control circuit 15 detects that the rack 143 has not moved. When the rack 143 moves from the initial position toward the final position, the second protrusion 1431B actuates the displacement sensor switch 1521 to generate the second third signal, and the control circuit 15 detects that the rack 143 has reached the first displacement. Subsequently, the third protrusion 1431C actuates the displacement sensor switch 1521 to generate the third third signal, and the control circuit 15 detects that the rack 143 has reached the second displacement. Subsequently, the fourth protrusion 1431D actuates the displacement sensor switch 1521 to generate the fourth third signal, and the control circuit 15 detects that the rack 143 has reached the third displacement. The plurality of loading units 30 are the first loading unit 30A, the second loading unit 30B, and the third loading unit 30C. The first displacement of the rack 143 corresponds to the firing stroke of the third loading unit 30C, the second displacement of the rack 143 corresponds to the firing stroke of the second loading unit 30B, and the third displacement of the rack 143 corresponds to the firing stroke of the first loading unit 30A. The handle assembly 11 includes the motor 141. The control circuit 15 is configured to control the motor 141 to drive the rack 143 to control the firing stroke of the loading unit 30. The first protrusion 1431A, the second protrusion 1431B, the third protrusion 1431C, and the fourth protrusion 1431D occupy minimal space, thus enabling the handle assembly 11 to save space.

In other embodiments, the method for operating a stapling surgical instrument includes: providing a handle assembly 11, a shaft assembly 20, and a plurality of loading units 30 with different staple line lengths; connecting the handle assembly 11 and the shaft assembly 20, wherein the handle assembly 11 includes a control circuit 15 provided with mounting sensor switches 1511 and a slider 18, and the shaft assembly 20 includes a sensing mechanism 29; releasably mounting any loading unit 30 to the shaft assembly 20, wherein the number of the mounting sensor switches 1511 is less than the number of staple line lengths of the loading units 30; pushing the slider 18 through the sensing mechanism 29 to actuate any mounting sensor switch 1511 to generate a first signal or not actuate it to generate a second signal; identifying whether the loading unit 30 is not mounted or identifying the staple line length of the loading unit 30 based on all combinations of the first signals or the second signals by the control circuit 15.

Specifically, the handle assembly 11 includes a rack 143 provided with a plurality of protrusions 1431, and the control circuit 15 further includes a displacement sensor switch 1521.

The method further includes: moving the rack 143 between the initial position and the final position, actuating the displacement sensor switch 1521 through the protrusions 1431 to generate a third signal or not actuating it to generate a fourth signal; sensing the initial position or the displacement of the rack 143 based on the number of the third signals by the control circuit 15, wherein the displacement of the rack 143 corresponds to a firing stroke of the loading unit 30. The handle assembly 11 further includes the motor 141. The method further includes using the control circuit 15 to control the motor 141 to drive the rack 143 to control the firing stroke of the loading unit 30.

As shown in FIG. 3 to FIG. 9, the shaft assembly 20 includes a firing rod 23, the firing rod 23, a sensing collar 24, and a main body 221 that are coaxially arranged, the main body 221 surrounds the sensing collar 24, and the sensing collar 24 surrounds the firing rod 23. A proximal end of the firing rod 23 is rotatably connected to a distal end of the rack 143. When the shaft assembly 20 rotates relative to the handle assembly 11, the firing rod 23 and the main body 221 rotate synchronously and rotate relative to the rack 143. When the motor 141 drives the rack 143 to move along the longitudinal axis x, the rack 143 drives the firing rod 23 to move between a proximal position and a distal position.

Figure 7:
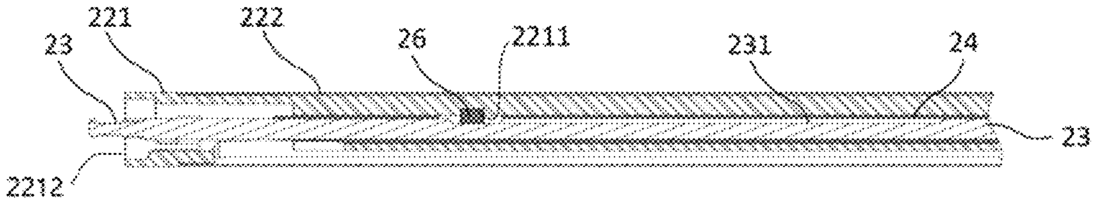
FIG. 7 is a cross-sectional view of the elongated body shown in FIG. 6.

As shown in FIG. 5 to FIG. 7, the shaft assembly 20 includes an anti-rotation pin 26, the main body 221 includes a keyway 2211, the firing rod 23 includes an anti-rotation surface 231, and the sensing collar 24 includes a first opening 241. The anti-rotation pin 26 is fixed to the keyway 2211, passes through the first opening 241, and engages with the anti-rotation surface 231 to prevent the firing rod 23 from rotating relative to the main body 221.

In an embodiment, the stapling surgical instrument 10 includes a handle assembly 11, a shaft assembly 20, and a loading unit 30. The shaft assembly 20 is rotatably connected to the handle assembly 11, and the loading unit 30 is releasably mounted to the shaft assembly 20. The shaft assembly 20 includes an elongated body 22, the firing rod 23, the sensing collar 24, and the anti-rotation pin 26, the elongated body 22 includes the main body 221, the firing rod 23 includes an anti-rotation surface 231, and the sensing collar 24 includes an opening 241. The main body 221 surrounds the sensing collar 24, the sensing collar 24 surrounds the firing rod 23, and the firing rod 23 is arranged around a longitudinal axis x. The anti-rotation pin 26 is fixed to the main body 221, passes through the opening 241, and engages with the anti-rotation surface 231 to prevent the firing rod 23 from rotating relative to the main body 221. When the shaft assembly 20 rotates by a certain angle relative to the handle assembly 11, the main body 221 drives the firing rod 23 to rotate by the certain angle, thus preventing the rotation of the shaft assembly 20 from affecting the normal operation of the firing rod 23.

The handle assembly 11 includes a drive assembly 14. The proximal end of the firing rod 23 is rotatably connected to a distal end of the drive assembly 14. When the anti-rotation pin 26 passes through the opening 241 and engages with the anti-rotation surface 231, the drive assembly 14 is configured to drive the firing rod 23 to move along the longitudinal axis x. Thus, the firing rod 23 can rotate together with the main body 221 and moving with the rack 143 between the proximal position and the distal position.

The dimension of the anti-rotation surface 231 along the longitudinal axis x is greater than a dimension of the anti-rotation pin 26 along the longitudinal axis x. When the firing rod 23 moves along the longitudinal axis x, the anti-rotation pin 26 is positioned between a proximal end and a distal end of the anti-rotation surface 231. Thus, the firing rod 23 can move between the proximal position and the distal position while avoiding rotation relative to the main body 221.

When the shaft assembly 20 rotates relative to the handle assembly 11, the main body 221, the firing rod 23, and the loading unit 30 rotate together. Thus, the firing rod 23 and the loading unit 30 can rotate with the main body 221 and operating normally.

The anti-rotation pin 26 engages with the first opening 241 to prevent the sensing collar 24 from rotating relative to the firing rod 23. Thus, the sensing collar 24 can rotate with the firing rod 23 and operating normally.

The dimension of the first opening 241 along the longitudinal axis x is greater than the dimension of the anti-rotation pin 26 along the longitudinal axis x. When the anti-rotation pin 26 prevents the sensing collar 24 from rotating relative to the firing rod 23, the loading unit 30 pushes the sensing collar 24 to move along the longitudinal axis x. Thus, the sensing collar 24 can rotate with the firing rod 23 and pushing a sensing sleeve 25 to move proximally.

The loading unit 30 is the first loading unit 30A or the second loading unit 30B, wherein a staple line length of the first loading unit 30A is different from a staple line length of the second loading unit 30B. The first loading unit 30A is releasably connected to the shaft assembly 20 and pushes the sensing collar 24 to a first sensing position. The second loading unit 30B is releasably connected to the shaft assembly 20 and pushes the sensing collar 24 to a second sensing position. Thus, a position of the sensing collar 24 can be used to identify the staple line length of the loading unit 30.

The shaft assembly 20 further includes a sensing sleeve 25, the handle assembly 11 further includes the control circuit 15 and the slider 18, and the control circuit 15 includes a sensing module 151. A proximal end of the sensing collar 24 contacts a distal end of the sensing sleeve 25, a proximal end of the sensing sleeve 25 contacts a distal end of the slider 18, and the sensing module 151 is configured to detect a position of the slider 18. Thus, the control circuit 15 can identify the staple line length of the loading unit 30.

The shaft assembly 20 further includes a rotating housing 21, and a proximal end of the main body 221 is fixed to a distal end of the rotating housing 21. The sensing sleeve 25 is located within the rotating housing 21. The sensing sleeve 25 is fixed relative to the rotating housing 21 in a circumferential direction about the longitudinal axis x, or the sensing sleeve 25 is fixed relative to the handle assembly 11 in the circumferential direction about the longitudinal axis x. Thus, when the shaft assembly 20 rotates relative to the handle assembly 11, the sensing sleeve 25 rotates relative to the handle assembly 11 or the shaft assembly 20.

A proximal end of the sensing sleeve 25 is provided with a flange 251. When the shaft assembly 20 rotates relative to the handle assembly 11, rotation of the sensing sleeve 25 is independent of a position of the slider 18. Thus, the flange 251 ensures that proximal movement of the sensing sleeve 25 changes the position of the slider 18 while preventing rotation of the sensing sleeve 25 from changing the position of the slider 18.

As shown in FIG. 13*a* to FIG. 13*d*, during the mounting of the loading unit 30 to the shaft assembly 20, a proximal end of the loading unit 30 is first inserted into a distal end of the shaft assembly 20. Then, the loading unit 30 rotates by a certain angle relative to the shaft assembly 20. Next, the loading unit 30 is locked to the shaft assembly 20. During a process of releasing the loading unit 30 from the shaft assembly 20, the loading unit 30 is first unlocked from the shaft assembly 20. Then, the loading unit 30 rotates by a certain angle relative to the shaft assembly 20. Next, the loading unit 30 is separated from the shaft assembly 20.

As shown in FIG. 7, FIG. 11, FIG. 13*a* to FIG. 13*d*, the distal end of the loading unit 30 includes an insertion portion 36 and a mounting boss 311, wherein the mounting boss 311 is mounted on the insertion portion 36. The proximal end of the insertion portion 36 and the mounting boss 311 are spaced apart by a first distance along the longitudinal axis x. In the shaft assembly 20, a proximal end of the main body 221 is provided with a notch 2212. When the loading unit 30 is mounted to the shaft assembly 20, the insertion portion 36 is inserted into the notch 2212. The insertion portion 36 rotates by a certain angle relative to the notch 2212. The mounting boss 311 is prevented from rotating relative to the main body 221. When the loading unit 30 is released from the shaft assembly 20, the mounting boss 311 is allowed to rotate relative to the main body 221. The insertion portion 36 rotates by a certain angle relative to the notch 2212. The insertion portion 36 is separated from the notch 2212.

As shown in FIG. 5 and FIG. 14*a* to FIG. 14*c*, the shaft assembly 20 includes a locking mechanism 28, the locking mechanism 28 including a locking slider 281, a locking member 282, and an elastic member 283. The locking slider 281 is movable along the longitudinal axis x between a proximal position and a distal position. The locking member 282 is rotatable between a first position and a second position. When the locking slider 281 moves to the distal position, the locking member 282 is allowed to remain in the first position or rotate to the second position. When the locking slider 281 moves to the proximal position, the locking slider 281 drives the locking member 282 to rotate to the first position or remain in the first position. The elastic member 283 is configured to resiliently return the locking slider 281 to the distal position.

As shown in FIG. 13*a* to FIG. 13*d*, the locking slider 281 is fixed relative to the main body 221 in a circumferential direction about the longitudinal axis x. When the locking slider 281 moves to the distal position, the locking slider 281 prevents the mounting boss 311 from rotating relative to the main body 221. When the locking slider 281 moves to the proximal position, the locking slider 281 allows the mounting boss 311 to rotate relative to the main body 221.

As shown in FIG. 14*a* to FIG. 14*c*, the firing rod 23 includes a groove 232, the sensing collar 24 includes a second opening 242, and the locking member 282 includes a locking portion 2821. When the locking member 282 is in the first position, the locking portion 2821 passes through the second opening 242 into the groove 232 and allows the sensing collar 24 to move proximally. When the locking member 282 is in the second position, the locking portion 2821 moves out of the second opening 242 and the groove 232, and allows the firing rod 23 to move distally.

As shown in FIG. 14*a* to FIG. 14*c*, when the loading unit 30 is mounted to or released from the shaft assembly 20, the firing rod 23 is not driven and remains in the proximal position. Even if the loading unit 30 is accidentally separated from the shaft assembly 20, the firing rod 23 is not driven and remains in the proximal position. When the loading unit 30 is locked to the shaft assembly 20, the firing rod 23 can be driven to move along the longitudinal axis x.

As shown in FIG. 13*a* to FIG. 14*c*, when the loading unit 30 is mounted to the shaft assembly 20, the insertion portion 36 is inserted into the notch 2212. The insertion portion 36 pushes the locking slider 281 to move to the proximal position. The locking slider 281 drives the locking member 282 to rotate to the first position or remain in the first position. The locking portion 2821 passes through the second opening 242 into the groove 232. The insertion portion 36 rotates by a certain angle relative to the notch 2212. The elastic member 283 resiliently returns the locking slider 281 to the distal position. The locking slider 281 prevents the mounting boss 311 from rotating relative to the main body 221.

As shown in FIG. 13*a* to FIG. 14*c*, when the loading unit 30 is locked to the shaft assembly 20, the drive assembly 14 drives the firing rod 23 to move to the distal position. The firing rod 23 drives the locking member 282 to rotate to the second position. The locking portion 2821 moves out of the second opening 242 and the groove 232. The locking member 282 prevents the locking slider 281 from moving to the proximal position. The locking slider 281 prevents the mounting boss 311 from rotating relative to the main body 221.

As shown in FIG. 13*a* to FIG. 14*c*, when the loading unit 30 is released from the shaft assembly 20, the user pushes the locking slider 281 to move to the proximal position. The locking slider 281 drives the locking member 282 to rotate to the first position or remain in the first position. The locking slider 281 allows the mounting boss 311 to rotate relative to the main body 221. The insertion portion 36 rotates by a certain angle relative to the notch 2212. The insertion portion 36 is separated from the notch 2212.

In an embodiment, the stapling surgical instrument 10 includes the shaft assembly 20 and the loading unit 30 releasably mounted to the shaft assembly 20. The shaft assembly 20 includes the firing rod 23 provided with the groove 232, the sensing collar 24 provided with the second opening 242, and the locking member 282 provided with the locking portion 2821. The firing rod 23 and the sensing collar 24 are arranged coaxially, and the locking member 282 is rotatable between the first position and the second position. When the locking member 282 rotates to the first position, the locking portion 2821 passes through the second opening 242 into the groove 232 and allows the sensing collar 24 to move proximally. When the locking member 282 rotates to the second position, the locking portion 2821 moves out of the second opening 242 and the groove 232, and allows the firing rod 23 to move distally. During the mounting of the loading unit 30 to the shaft assembly 20, the locking member 282 in the first position does not prevent the sensing collar 24 from moving. The movement of the sensing collar 24 can be used to identify the staple line length of the loading unit 30. When the loading unit 30 is locked to the shaft assembly 20, the locking member 282 allows the firing rod 23 to operate normally.

The firing rod 23 further includes the anti-rotation surface 231, and the sensing collar 24 further includes the first opening 241. The shaft assembly 20 further includes the anti-rotation pin 26. The anti-rotation pin 26 is fixedly arranged to pass through the first opening 241 and engages with the anti-rotation surface 231. Thus, the firing rod 23 is prevented from rotating relative to the main body 221.

The anti-rotation surface 231 and the groove 232 are offset by more than 30 degrees in a circumferential direction of the firing rod 23. The first opening 241 and the second opening 242 are offset by more than 30 degrees in a circumferential direction of the sensing collar 24. The anti-rotation surface 231 is aligned with the first opening 241, and the groove 232 is aligned with the second opening 242. Thus, when the firing rod 23 or the sensing collar 24 moves along the longitudinal axis x, the anti-rotation surface 231 and the second opening 242 are misaligned, and the groove 232 and the first opening 241 are misaligned.

The loading unit 30 is the first loading unit 30A or the second loading unit 30B, wherein the staple line length of the first loading unit 30A is different from the staple line length of the second loading unit 30B. When the first loading unit 30A is mounted to the shaft assembly 20, the sensing collar 24 moves to the first sensing position, and the groove 232 and the second opening 242 are aligned. When the second loading unit 30B is mounted to the shaft assembly 20, the sensing collar 24 moves to the second sensing position, and the groove 232 and the second opening 242 are aligned. Thus, whether the sensing collar 24 moves to the first sensing position or the second sensing position, the locking member 282 can rotate to the first position or remain in the first position. Simultaneously, the movement of the sensing collar 24 can be used to identify the staple line length of the first loading unit 30A or the second loading unit 30B.

The anti-rotation pin 26 engages with the first opening 241 to restrict the sensing collar 24 from rotating relative to the firing rod 23. Simultaneously, the groove 232 and the second opening 242 are aligned. Thus, even if the sensing collar 24 rotates slightly relative to the firing rod 23, the locking member 282 can rotate to the first position or remain in the first position.

The shaft assembly 20 further includes the locking slider 281, the locking slider 281 being movable along the longitudinal axis x. When the loading unit 30 is mounted to the shaft assembly 20, the loading unit 30 pushes the sensing collar 24 to move proximally and pushes the locking slider 281 to move to the proximal position. Simultaneously, the locking slider 281 drives the locking member 282 to rotate to the first position or remain in the first position. Thus, when the locking slider 281 moves to the proximal position, the locking slider 281 allows the mounting boss 311 to rotate relative to the main body 221. Simultaneously, the movement of the sensing collar 24 can be used to identify the staple line length of the loading unit 30.

When the loading unit 30 is released from the shaft assembly 20, the locking slider 281 moves to the distal position, and the sensing collar 24 moves distally. Simultaneously, the locking slider 281 allows the locking member 282 to remain in the first position or rotate to the second position. Thus, when the locking slider 281 moves to the distal position, the locking slider 281 prevents the mounting boss 311 from rotating relative to the main body 221. Simultaneously, the movement of the sensing collar 24 can be used to detect that the loading unit 30 is not mounted of the loading unit 30.

The shaft assembly 20 further includes the main body 221, and the loading unit 30 further includes the mounting boss 311. When the locking slider 281 moves to the proximal position, the locking slider 281 allows the mounting boss 311 to rotate relative to the main body 221, thereby unlocking the loading unit 30. When the locking slider 281 moves to the distal position, the locking slider 281 prevents the mounting boss 311 from rotating relative to the main body 221, thereby locking the loading unit 30. Thus, when the loading unit 30 is unlocked from the shaft assembly 20, the loading unit 30 starts to be released from the shaft assembly 20. When the loading unit 30 is locked to the shaft assembly 20, the loading unit 30 completes its mounting to the shaft assembly 20.

The stapling surgical instrument 10 further includes the handle assembly 11 connected to the shaft assembly 20, the handle assembly 11 including the control circuit 15 provided with a mounting sensor module 151 and the slider 18. When the loading unit 30 is mounted to the shaft assembly 20, the mounting sensor module 151 can detect the position of the slider 18 to identify the staple line length of the loading unit 30.

The handle assembly 11 further includes the rack 143 connected to the firing rod 23, and the control circuit 15 further includes a displacement sensor module 152. When the firing rod 23 moves with the rack 143, the displacement sensor module 152 detects an initial position or displacement of the rack 143, thereby enabling the control circuit 15 to control a firing stroke of the loading unit 30.

Figure 11:
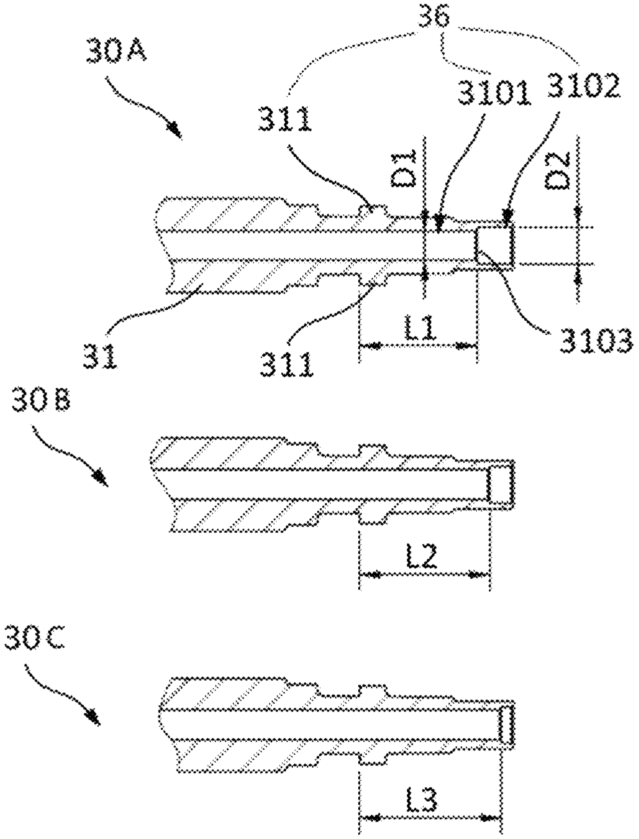
FIG. 11 is a cross-sectional view of the loading unit shown in FIG. 10.
Figure 12:
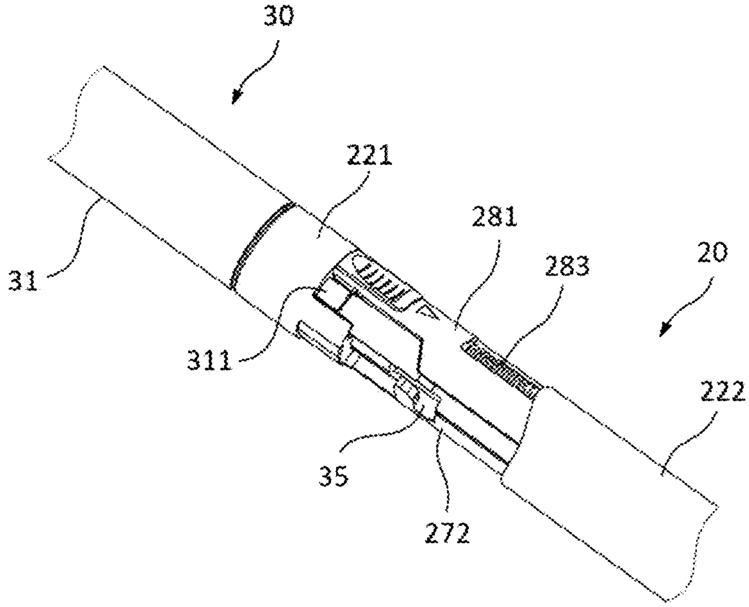
FIG. 12 is an exemplary partial perspective view of the loading unit mounting.

As shown in FIG. 10 to FIG. 11, the insertion portion 36 includes a first lumen 3101 and a second lumen 3102, wherein the first lumen 3101 or the second lumen 3102 may be a circular lumen, a square lumen, or a polygonal lumen. The first lumen 3101 and the second lumen 3102 intersect with each other. When the insertion portion 36 is inserted into the notch 2212, the second lumen 3102 has a second dimension D2 to accommodate a distal end of the firing rod 23 and a distal end of the sensing collar 24, and the first lumen 3101 has a first dimension D1 to accommodate the distal end of the firing rod 23.

As shown in FIG. 10 to FIG. 11 and FIG. 15 to FIG. 17, in the loading unit 30, the intersection of the first lumen 3101 and the second lumen 3102 defines the working surface 3103, and the mounting boss 311 and the working surface 3103 are spaced apart by a second distance along the longitudinal axis x. The second distance is set according to the staple line length. The second distance of the loading unit 30 determines a displacement by which the working surface 3103 drives a sensing mechanism 29 to push the slider 18.

As shown in FIG. 10 to FIG. 11 and FIG. 15 to FIG. 17, in the first loading unit 30A, the staple line length is 60 millimeters, and the second distance is set to L1. When the first loading unit 30A is mounted to the shaft assembly 20, the working surface 3103 drives the sensing mechanism 29 to push the slider 18 to move by a displacement L1'. In the second loading unit 30B, the staple line length is 45 millimeters, and the second distance is set to L2, wherein L2 is greater than L1. When the second loading unit 30B is mounted to the shaft assembly 20, the working surface 3103 drives the sensing mechanism 29 to push the slider 18 to move by a displacement L2', wherein L2' is greater than L1'. In the third loading unit 30C, the staple line length is 30 millimeters, and the second distance is set to L3, wherein L3 is greater than L2. When the third loading unit 30C is mounted to the shaft assembly 20, the working surface 3103 drives the sensing mechanism 29 to push the slider 18 to move by a displacement L3', wherein L3' is greater than L2'.

In an embodiment, the stapling surgical instrument 10 includes the shaft assembly 20 and the loading unit 30. The shaft assembly 20 includes the main body 221, the firing rod 23, and the sensing collar 24. The main body 221 surrounds the sensing collar 24, the sensing collar 24 directly surrounds the firing rod 23, and the firing rod 23 extends along the longitudinal axis x. The distal end of the main body 221 is provided with the notch 2212. The loading unit 30 includes the insertion portion 36. The insertion portion 36 is provided with the mounting boss 311, the first lumen 3101, and the second lumen 3102. The proximal end of the insertion portion 36 and the mounting boss 311 are spaced apart by a first distance along the longitudinal axis x. The first lumen 3101 and the second lumen 3102 intersect with each other. When the loading unit 30 is releasably mounted to the shaft assembly 20, the insertion portion 36 is inserted into the notch 2212, wherein the second lumen 3102 has a second dimension D2 to accommodate a distal end of the firing rod 23 and a distal end of the sensing collar 24, and the first lumen 3101 has a first dimension D1 to accommodate the distal end of the firing rod 23. When the loading unit 30 rotates with the shaft assembly 20, the firing rod 23 and the sensing collar 24 also rotate. The second lumen 3102 accommodates the distal end of the firing rod 23 and the distal end of the sensing collar 24, the firing rod 23 and the sensing collar 24 being arranged adjacent to each other, with other components omitted in between to simplify the rotation of the shaft assembly 20. Although different loading units 30 have different staple line lengths, the proximal end of the insertion portion 36 and the mounting boss 311 are spaced apart by a certain first distance along the longitudinal axis x. When different loading units 30 are locked to the shaft assembly 20, each insertion portion 36 can be fixed to the same notch 2212.

Different loading units 30 have different staple line lengths. The intersection of the first lumen 3101 and the second lumen 3102 defines the working surface 3103, and the mounting boss 311 and the working surface 3103 are spaced apart by a second distance along the longitudinal axis x. The second distance is set according to the staple line length. Thus, when different loading units 30 are mounted to the shaft assembly 20, the working surface 3103 can be used to identify the staple line length of the loading unit 30.

The stapling surgical instrument 10 further includes the handle assembly 11, the handle assembly 11 including the control circuit 15 and the slider 18, the control circuit 15 including the mounting sensor module 151, and the shaft assembly 20 further including the sensing mechanism 29. When the loading unit 30 is mounted to the shaft assembly 20, the working surface 3103 drives the sensing mechanism 29 to push the slider 18, the mounting sensor module 151 detects a position of the slider 18, and the control circuit 15 identifies the staple line length of the loading unit 30. Thus, when different loading units 30 have different staple line lengths, the working surface 3103 drives the sensing mechanism 29 to push the slider 18 to different positions to identify the staple line length of the loading unit 30.

The handle assembly 11 further includes the drive assembly 14, the drive assembly 14 including the rack 143, and the control circuit 15 further including the displacement sensor module 152. When the loading unit 30 is mounted to the shaft assembly 20, the control circuit 15 controls the drive assembly 14 to drive the firing rod 23, and the displacement sensor module 152 detects a displacement of the rack 143, thereby enabling the control circuit 15 to control a firing stroke of the loading unit 30. Thus, when different loading units 30 have different staple line lengths, the control circuit 15 can control the firing stroke of the loading unit 30.

The shaft assembly 20 further includes a bending control mechanism 27, and the loading unit 30 further includes a jaw assembly 32 and a second bending control rod 35. The insertion portion 36 further includes a narrow slot 312, the narrow slot 312 passing through sidewalls of the first lumen 3101 and the second lumen 3102. The second bending control rod 35 is disposed in the narrow slot 312. When the loading unit 30 is mounted to the shaft assembly 20, the bending control mechanism 27 can drive the second bending control rod 35, enabling the jaw assembly 32 to bend. Thus, the second bending control rod 35 is movable within the narrow slot 312 to avoid affecting components in the first lumen 3101 and the second lumen 3102.

The shaft assembly 20 further includes the locking slider 281 and the elastic member 283. During the mounting of the loading unit 30 to the shaft assembly 20, when the insertion portion 36 pushes the locking slider 281 to move to the proximal position, the locking slider 281 allows the mounting boss 311 to rotate relative to the main body 221. When the elastic member 283 resiliently returns the locking slider 281 to the distal position, the locking slider 281 prevents the mounting boss 311 from rotating relative to the main body 221. Thus, the loading unit 30 is locked to the shaft assembly 20.

The loading unit 30 is the first loading unit 30A or the second loading unit 30B, and the mounting sensor module 151 includes a first mounting sensor switch 1511A and a second mounting sensor switch 1511B. The staple line length of the first loading unit 30A is greater than the staple line length of the second loading unit 30B. When the first loading unit 30A is mounted to the shaft assembly 20, the slider 18 actuates the first mounting sensor switch 1511A and does not actuate the second mounting sensor switch 1511B, thereby enabling the control circuit 15 to identify the staple line length of the first loading unit 30A. When the second loading unit 30B is mounted to the shaft assembly 20, the slider 18 does not actuate the first mounting sensor switch 1511A and actuates the second mounting sensor switch 1511B, thereby enabling the control circuit 15 to identify the staple line length of the second loading unit 30B. Thus, the actuation of the mounting sensor switches can be used to identify the staple line length of the loading unit 30.

The displacement sensor module 152 includes a first displacement sensor switch 1521A, a second displacement sensor switch 1521B, a third displacement sensor switch 1521C, and a fourth displacement sensor switch 1521D. When the first loading unit 30A is mounted to the shaft assembly 20, the rack 143 actuates the first displacement sensor switch 1521A when in an initial position. The rack 143 moves a first displacement to actuate the second displacement sensor switch 1521B. The rack 143 moves a second displacement to actuate the third displacement sensor switch 1521C. The rack 143 moves a third displacement to actuate the fourth displacement sensor switch 1521D. The control circuit 15 controls the firing stroke of the first loading unit 30A. Thus, the actuation of the displacement sensor switches can be used to control the firing stroke of the loading unit 30.

The loading unit 30 includes the insertion portion 36. The insertion portion 36 is provided with a mounting boss 311, a first lumen 3101, and a second lumen 3102. The proximal end of the insertion portion 36 and the mounting boss 311 are spaced apart by a first distance along the longitudinal axis x. The first lumen 3101 and the second lumen 3102 intersect with each other. The loading unit 30 is releasably mounted to the shaft assembly 20. The shaft assembly 20 includes the main body 221, the firing rod 23, and the sensing collar 24. The main body 221 surrounds the sensing collar 24, the sensing collar 24 directly surrounds the firing rod 23, and the firing rod 23 extends along the longitudinal axis x. The distal end of the main body 221 is provided with the notch 2212. When the insertion portion 36 is inserted into the notch 2212, the second lumen 3102 has a second dimension D2 to accommodate a distal end of the firing rod 23 and a distal end of the sensing collar 24, and the first lumen 3101 has a first dimension D1 to accommodate the distal end of the firing rod 23.

The loading units 30 have different staple line lengths. The intersection of the first lumen 3101 and the second lumen 3102 defines the working surface 3103, and the mounting boss 311 and the working surface 3103 are spaced apart by a second distance along the longitudinal axis x. The second distance is set according to the staple line length.

Overall, the stapling surgical instrument 10 can identify the staple line length of the loading unit 30 and control a firing stroke. When the first loading unit 30A is mounted to the shaft assembly 20, the working surface 3103 drives the sensing mechanism 29 to push the slider 18 to move. The mounting sensor module 151 detects a position of the slider 18. The control circuit 15 identifies the staple line length of the first loading unit 30A as 60 millimeters. When a user presses the forward button 171, the control circuit 15 controls the drive assembly 14 to drive the firing rod 23 to move distally. The displacement sensor module 152 detects a displacement of the rack 143. The control circuit 15 controls the firing stroke of the loading unit 30. When the displacement sensor module 152 detects that the rack 143 reaches a third displacement, the control circuit 15 stops the drive assembly 14 from driving the firing rod 23 to move. When the user releases the forward button 171, the control circuit 15 controls the drive assembly 14 to drive the firing rod 23 to move proximally. Optionally, when a user presses the reverse button 172, the control circuit 15 controls the drive assembly 14 to drive the firing rod 23 to move proximally. When the displacement sensor module 152 detects that the rack 143 returns to an initial position, the control circuit 15 stops the drive assembly 14 from driving the firing rod 23 to move. When the first loading unit 30A is released from the shaft assembly 20, the second loading unit 30B or the third loading unit 30C can be mounted to the shaft assembly 20 and operate similarly.

It is apparent that the embodiments above of the present disclosure are merely examples provided for clearly illustrating the present disclosure, and are not intended to limit the present disclosure. For those of ordinary skill in the art, other variations or modifications in different forms may be made based on the above description. It is neither necessary nor possible to exhaustively enumerate all embodiments herein. Any modifications, equivalent substitutions, improvements, and the like made within the spirit and principles of the present disclosure shall be included within the scope of protection of the claims of the present disclosure.

What is claimed is:

1. A stapling surgical instrument comprising a handle assembly (11), a shaft assembly (20), and a plurality of loading units (30) with different staple line lengths;

wherein the handle assembly (11) comprises a control circuit (15) provided with mounting sensor switches (1511) and a slider (18), the shaft assembly (20) comprises a sensing mechanism (29), and any one of the loading units (30) is configured to be releasably mounted to the shaft assembly (20);

the number of the mounting sensor switches (1511) is less than the number of staple line lengths of the loading units (30);

a mounting of the loading unit (30) is configured to drive the sensing mechanism (29) to push the slider (18), the slider (18) is configured to actuate any one of the mounting sensor switches (1511) to generate a first signal or to not actuate to generate a second signal, and the control circuit (15) is configured to identify whether the loading unit (30) is not mounted or identifies the staple line length based on all combinations of the first signals and the second signals.

2. The stapling surgical instrument according to claim 1, wherein the handle assembly (11) further comprises a rack (143) provided with a plurality of protrusions (1431), and the control circuit (15) further comprises a displacement sensor switch (1521);

the rack (143) is movable between an initial position and an end position, the protrusions (1431) are configured to actuate the displacement sensor switch (1521) to generate a third signal or to not actuate to generate a fourth signal, the control circuit (15) is configured to sense the initial position or displacement of the rack (143) based on the number of the third signals, wherein the displacement of the rack (143) corresponds to a firing stroke of the loading unit (30).

3. The stapling surgical instrument according to claim 2, wherein the plurality of protrusions (1431) comprise a first protrusion (1431A), a second protrusion (1431B), a third protrusion (1431C), and a fourth protrusion (1431D);

when the rack (143) is at the initial position, the first protrusion (1431A) actuates the displacement sensor switch (1521) to generate a first one of the third signals, and the control circuit (15) senses that the rack (143) has not moved;

when the rack (143) moves from the initial position toward the end position, the second protrusion (1431B) actuates the displacement sensor switch (1521) to generate a second one of the third signals, and the control circuit (15) senses that the rack (143) has reached a first displacement;

subsequently, the third protrusion (1431C) actuates the displacement sensor switch (1521) to generate a third one of the third signals, and the control circuit (15) senses that the rack (143) has reached a second displacement;

subsequently, the fourth protrusion (1431D) actuates the displacement sensor switch (1521) to generate a fourth one of the third signals, and the control circuit (15) senses that the rack (143) has reached a third displacement.

4. The stapling surgical instrument according to claim 3, wherein the plurality of loading units (30) comprise a first loading unit (30A), a second loading unit (30B), and a third loading unit (30C);

the first displacement of the rack (143) corresponds to a firing stroke of the third loading unit (30C), the second displacement of the rack (143) corresponds to a firing stroke of the second loading unit (30B), and the third displacement of the rack (143) corresponds to a firing stroke of the first loading unit (30A).

5. The stapling surgical instrument according to claim 2, wherein the handle assembly (11) further comprises a motor (141);

the control circuit (15) is configured to control the motor (141) to drive the rack (143) so as to control a firing stroke of the loading unit (30).

6. The stapling surgical instrument according to claim 1, wherein the mounting sensor switch (1511) comprises a first switch (1511A) and a second switch (1511B);

when the loading unit (30) is released from the shaft assembly (20), the slider (18) does not actuate the first switch (1511A) and the second switch (1511B), and the control circuit (15) senses that the loading unit (30) is not mounted.

7. The stapling surgical instrument according to claim 6, wherein the plurality of loading units (30) comprise a first loading unit (30A), a second loading unit (30B), and a third loading unit (30C);

when the first loading unit (30A) is mounted to the shaft assembly (20), the slider (18) actuates the first switch (1511A) and does not actuate the second switch (1511B), and the control circuit (15) identifies the staple line length of the first loading unit (30A);

when the second loading unit (30B) is mounted to the shaft assembly (20), the slider (18) actuates the first switch (1511A) and actuates the second switch (1511B), and the control circuit (15) identifies the staple line length of the second loading unit (30B);

when the third loading unit (30C) is mounted to the shaft assembly (20), the slider (18) does not actuate the first switch (1511A) and actuates the second switch (1511B), and the control circuit (15) identifies the staple line length of the third loading unit (30C).

8. A method for operating a stapling surgical instrument, wherein the method comprises:

providing a handle assembly (11), a shaft assembly (20), and a plurality of loading units (30) with different staple line lengths;

connecting the handle assembly (11) to the shaft assembly (20), wherein the handle assembly (11) comprises a control circuit (15) provided with mounting sensor switches (1511) and a slider (18), and the shaft assembly (20) comprises a sensing mechanism (29);

releasably mounting any one of the loading units (30) to the shaft assembly (20), wherein the number of the mounting sensor switches (1511) is less than the number of staple line lengths of the loading units (30);

pushing the slider (18) through the sensing mechanism (29) to actuate any one of the mounting sensor switches (1511) to generate a first signal or not to actuate to generate a second signal;

identifying whether the loading unit (30) is not mounted or identifying the staple line length of the loading unit (30) based on all combinations of the first signals and the second signals by the control circuit (15).

9. The method according to claim 8, wherein the handle assembly (11) further comprises a rack (143) provided with a plurality of protrusions (1431), and the control circuit (15) further comprises a displacement sensor switch (1521);

the method further comprises: moving the rack (143) between an initial position and an end position, actuating the displacement sensor switch (1521) through the protrusions (1431) to generate a third signal or not actuating to generate a fourth signal;

sensing the initial position or the displacement of the rack (143) based on the number of the third signals by the control circuit (15), wherein the displacement of the rack (143) corresponds to a firing stroke of the loading unit (30).

10. The method according to claim 9, wherein the handle assembly (11) further comprises a motor (141);

the method further comprises using the control circuit (15) to control the motor (141) to drive the rack (143) to control a firing stroke of the loading unit (30).

* * * * *